US009456784B2

(12) United States Patent
Helekar et al.

(10) Patent No.: US 9,456,784 B2
(45) Date of Patent: Oct. 4, 2016

(54) METHOD AND APPARATUS FOR PROVIDING TRANSCRANIAL MAGNETIC STIMULATION (TMS) TO A PATIENT

(71) Applicants: The Methodist Hospital, Houston, TX (US); Cornell University, Ithaca, NY (US)

(72) Inventors: Santosh A. Helekar, Sugar Land, TX (US); Henning U. Voss, New York, NY (US)

(73) Assignees: The Methodist Hospital, Houston, TX (US); Cornell University, Ithaca, NY (US)

( * ) Notice: Subject to any disclaimer, the term of this patent is extended or adjusted under 35 U.S.C. 154(b) by 287 days.

(21) Appl. No.: 13/829,349

(22) Filed: Mar. 14, 2013

(65) Prior Publication Data
US 2014/0276182 A1    Sep. 18, 2014

(51) Int. Cl.
*A61N 1/00* (2006.01)
*A61B 5/00* (2006.01)
(Continued)

(52) U.S. Cl.
CPC ........... *A61B 5/6803* (2013.01); *A61B 5/0476* (2013.01); *A61N 2/006* (2013.01); *A61B 5/4836* (2013.01); *A61N 2/12* (2013.01)

(58) Field of Classification Search
CPC  A61B 5/6803; A61B 5/0476; A61B 5/4836; A61N 2/12; A61N 2/006; A61N 2/02; A61N 2/004; A61N 2/06
USPC ................................. 600/13, 14, 15, 9, 544
See application file for complete search history.

(56) References Cited

U.S. PATENT DOCUMENTS 4,967,038 A * 10/1990 Gevins ................. A61B 5/0017
                                                            600/383
6,488,617 B1 * 12/2002 Katz .................... A61B 5/0482
                                                            600/26
(Continued)

FOREIGN PATENT DOCUMENTS

DE    102011050507    11/2012
WO    WO 2009/036040    3/2009

OTHER PUBLICATIONS

Beauchamp, M. S. et al., fMRI-Guided Transcranial Magnetic Stimulation Reveals That the Superior Temporal Sulcus is a Cortical Locus of the McGurk Effect, The Journal of Neuroscience, 2010, 30(7): 2414-7.
(Continued)

*Primary Examiner* — Navin Natnithithadha
*Assistant Examiner* — Sunita Reddy
(74) *Attorney, Agent, or Firm* — Pandiscio & Pandiscio (57) ABSTRACT

Apparatus for applying Transcranial Magnetic Stimulation (TMS) to a patient, the apparatus including a head mount for disposition on the head of a patient; and a plurality of magnet assemblies for releasable mounting on the head mount, wherein each of the magnet assemblies includes a magnet for selectively providing a rapidly changing magnetic field capable of inducing weak electric currents in the brain of a patient so as to modify the natural electrical activity of the brain of the patient; wherein the number of magnet assemblies mounted on the head mount, their individual positioning on the head mount, and their selective provision of a rapidly changing magnetic field is selected so as to allow the spatial, strength and temporal characteristics of the magnetic field to be custom tailored for each patient, whereby to provide patient-specific TMS therapy, to assist in diagnosis or to map out brain function in neuroscience research.

21 Claims, 7 Drawing Sheets

(51) Int. Cl.
    *A61B 5/0476*    (2006.01)
    *A61N 2/00*    (2006.01)
    *A61N 2/12*    (2006.01)

(56) References Cited

U.S. PATENT DOCUMENTS

| | | | |
|---|---|---|---|
| 7,013,177 B1* | 3/2006 | Whitehurst | A61N 1/36071 607/46 |
| 2002/0151760 A1 | 10/2002 | Paturu | |
| 2004/0193001 A1* | 9/2004 | Miller | A61N 2/008 600/9 |
| 2006/0015153 A1 | 1/2006 | Gliner et al. | |
| 2006/0265022 A1* | 11/2006 | John | A61N 1/36139 607/45 |
| 2007/0093706 A1* | 4/2007 | Gevins | A61B 5/0478 600/383 |
| 2008/0014285 A1 | 1/2008 | Di Mauro et al. | |
| 2008/0312706 A1 | 12/2008 | Zangen et al. | |
| 2009/0082690 A1 | 3/2009 | Phillips et al. | |
| 2010/0185042 A1 | 7/2010 | Schneider et al. | |
| 2010/0210894 A1 | 8/2010 | Pascual-Leone et al. | |
| 2010/0249488 A1 | 9/2010 | Kardos et al. | |
| 2011/0034822 A1 | 2/2011 | Phillips et al. | |
| 2011/0105826 A1 | 5/2011 | Mishelevich et al. | |
| 2011/0112427 A1 | 5/2011 | Phillips et al. | |
| 2011/0118536 A1 | 5/2011 | Phillips et al. | |
| 2011/0118636 A1 | 5/2011 | Kitamura et al. | |
| 2011/0184223 A1 | 7/2011 | Peterchev et al. | |
| 2011/0270345 A1 | 11/2011 | Johnston et al. | |
| 2012/0157752 A1* | 6/2012 | Nishikawa | A61B 5/05 600/15 |
| 2014/0276182 A1 | 9/2014 | Helekar et al. | |

OTHER PUBLICATIONS

Beckers, G. et al., Cerebral visual motion blindness: transitory akinetopsia induced by transcranial magnetic stimulation of human area V5, Proceedings: Biological Sciences, 1992, 249(1325): 173-8.

Buch, E. R. et al., Noninvasive Associative Plasticity Induction in a Corticocortical Pathway of the Human Brain, The Journal of Neuroscience, 2011, 31(48): 17669-79.

De Pasquale et al., A Cortical Core for Dynamic Integration of Functional Networks in the Resting Human Brain, Neuron, 2012, 74(4): 753-64.

De Ridder, D. et al., Primary and Secondary Auditory Cortex Stimulation for Intractable Tinnitus, ORL, 2006, 68(1): 48-54.

Deco, G. et al., Ongoing Cortical Activity at Rest: Criticality, Multistability, and Ghost Attractors, The Journal of Neuroscience, 2012, 32(10): 3366-75.

Dell'Osso, B. et al., Meta-Review of Metanalytic Studies with Repetitive Transcranial Magnetic Stimulation (rTMS) for the Treatment of Major Depression, Clinical Practice & Epidemiology in Mental Health, 2011, 7, 167-77.

Devlin, J. T. et al., Stimulating language: insights from TMS, Brain, 2007, 130, 610-22.

Fox, M. D. et al., The human brain is intrinsically organized into dynamic, anticorrelated functional networks, Proceedings of the National Academy of Sciences of the USA, 2005, vol. 102, No. 27, 9673-8.

Guse, B. et al., Cognitive effects of high-frequency repetitive transcranial magnetic stimulation: a systematic review, Journal of Neural Transmission, 2010, 117: 105-22.

Huerta, P. T. et al., Transcranial magnetic stimulation, synaptic plasticity and network oscillations, Journal of NeuroEngineering and Rehabilitation, 2009, 6:7.

Kammer, T., Masking visual stimuli by transcranial magnetic stimulation, Psychological Research, 2007, 71: 659-66.

Lipton, R. B. et al., Transcranial Magnetic Simulation in the Treatment of Migraine, Neurotherapeutics: The Journal of the American Society for Experimental NeuroTherapeutics, 2010, vol. 7, 204-12.

Muller, P. A. et al., Safety and tolerability of repetitive transcranial magnetic stimulation in patients with pathologic positive sensory phenomena: a review of literature, Brain Stimulation, 2012, 5(3): 320-329.

Müller-Dahlhaus, F. et al., Plasticity resembling spike-timing dependent synaptic plasticity: the evidence in human cortex, Frontiers in Synaptic Neuroscience, 2010, vol. 2, Article 34, 1-11.

Pitcher, D. et al., Transcranial Magnetic Stimulation Disrupts the Perception and Embodiment of Facial Expressions, The Journal of Neuroscience, 2008, 28(36): 8929-33.

Rossi S. et al., Safety, ethical considerations, and application guidelines for the use of transcranial magnetic stimulation in clinical practice and research, Clinical Neurophysiology, 2009, 2008-2039.

Wassermann, E. M., Risk and safety of repetitive transcranial magnetic stimulation: report and suggested guidelines from the International Workshop on the Safety of Repetitive Transcranial Magnetic Stimulation, Jun. 5-7, 1996, Electroencephalography and Clinical Neurophysiology, 1998, 108, 1-16.

Wassermann, E. M. et al., Transcranial Magnetic Brain Stimulation: Therapeutic Promises and Scientific Gaps, Pharmacology and Therapeutics, 2012, 133(1): 98-107.

Amassian, V. E et al., Transcranial Magnetic Stimulation in Study of the Visual Pathway, Journal of Clinical Neurophysiology, 1998, 15(4): 288-304.

Azañón, E. et al., Somatosensory processing and body representation, Cortex 45, 2009, 1078-1084.

Delvendahl, I. et al., Plasticity of motor threshold and motor-evoked potential amplitude—A model of intrinsic and synaptic plasticity in human motor cortex?, Brain Stimulation 5, 2012, 586-593.

Fitzgerald, P. B. et al., GABA and cortical inhibition in motor and non-motor regions using combined TMS-EEG: A time analysis, Clinical Neurophysiology 120, 2009, 1706-1710.

Ilic, T. V. et al., Exploring Motor Cortical Plasticity Using Transcranial Magnetic Stimulation in Humans, Annals of the New York Academy of Sciences, 2005, vol. 1048(1): 175-184.

Kamitani, Y. et al., Manifestation of scotomas created by transcranial magnetic stimulation of human visual cortex, Nature Neuroscience, 1999, 2(8): 767-71.

Kamke, M. R. et al., Parietal disruption alters audiovisual binding in the sound-induced flash illusion, NeuroImage 62, 2012, 1334-1341.

Leuchter, A. F. et al., Synchronized Transcranial Magnetic Stimulation (sTMS) Efficacy and Safety of Low-field Synchronized Transcranial Magnetic Stimulation (sTMS) for Treatment of Major Depression, Brain Stimulation, 2015, 1-8.

Levasseur-Moreau, J. et al., Translational application of neuromodulation of decision-making, Brain Stimulation 5, 2012, 77-83.

Nakatani-Enomoto, S. et al., Bidirectional modulation of sensory cortical excitability by quadripulse transcranial magnetic stimulation (QPS) in humans, Clinical Neurophysiology 123, 2012, 1415-1421.

Sandrini, M. et al., The use of transcranial magnetic stimulation in cognitive neuroscience: A new synthesis of methodological issues, Neuroscience and Biobehavioral Reviews 35, 2011, 516-536.

Helekar, Santosh A., On the Possibility of Universal Neural Coding of Subjective Experience, Consciousness and Cognition, Dec. 1999, pp. 423-446, vol. 8, Issue 4.

Helekar Santosh A., In Defense of Experience—Coding Nonarbitrary Temporal Neural Activity Patterns, Consciousness and Cognition, Dec. 1999, pp. 455-461, vol. 8, issue 4.

Sanchez, Alvaro et al., Antimagnets: Controlling Magnetic Fields With Superconductor—Metamaterial Hybrids, New Journal of Physics, 2011, vol. 13.

Davan, Eran et al., Noninvasive brain stimulation: from physiology to network dynamics and back, Nature Neuroscience, Jul. 2013, vol. 16, No. 7.

Helekar, S.A. et al., Electromyographic motor-evoked potentials elicited by transcranial magnetic stimulation with rapidly moving permanent magnets mounted on a multisite stimulator cap, Presentation Abstract, Nov. 13, 2013.

* cited by examiner

COMPARISON OF PRESENT INVENTION WITH CONVENTIONAL TMS

| | Present Invention | Conventional TMS |
|---|---|---|
| Type of Magnet | Permanent Neodymium | Electromagnetic Coil |
| Maximum Field Strength | 1.48 T | 2.2 T |
| dB/dt | 500 - 5000 T/s | 5000 - 20,000 T/s |
| Stimulus Duration | 1 - 100 ms | 0.3 - 5 ms |
| Repetition Rate | 0.1 - 2 Hz | 0.1 - 50 Hz |
| Stimulation Sites | Multiple (1 - 32) | Single |
| Dynamic Modulation | Present | Absent |
| User Interaction | Present | Absent |
| Current for Stimulation | None | 4000 A |
| Power Supply | DC Battery (9 - 12 V) | AC Main (110 - 220 V) |
| Risk of Electric Shock | Absent | Present |
| Risk of Burns | Absent | Present |
| Risk of Seizure | Absent | Present at high rates |

METHOD AND APPARATUS FOR PROVIDING TRANSCRANIAL MAGNETIC STIMULATION (TMS) TO A PATIENT

FIELD OF THE INVENTION

This invention relates to Transcranial Magnetic Stimulation (TMS) in general, and more particularly to novel methods and apparatus for providing transcranial magnetic stimulation to a patient.

BACKGROUND OF THE INVENTION

Transcranial Magnetic Stimulation (TMS) is a non-invasive procedure in which magnetic stimulation is applied to the brain in order to modify the natural electrical activity of the brain, whereby to provide therapy to a patient, to assist in diagnosis or to map out brain function in neuroscience research. More particularly, TMS applies a rapidly changing magnetic field to the brain of a patient in order to induce weak electric currents in the brain of the patient through electromagnetic induction. These weak electric currents modify the natural electrical activity of the brain of the patient, whereby to provide therapy to the patient, to assist in diagnosis or to map out brain function in neuroscience research. TMS has been approved by the Food and Drug Administration (FDA) for treating depression. TMS is also currently being investigated in the management of various other neurological and psychiatric disorders, including stroke, migraines, Parkinson's disease, tinnitus, autism, schizophrenia, etc. TMS is also being used to study brain function in neuroscience research.

Conventional TMS apparatus generally comprises an electromagnetic coil which is fixed in position relative to the head of the patient. Since the magnetic field applied to the patient is a function of the configuration of the electromagnetic coil, the current passed through the electromagnetic coil, and the location of the electromagnetic coil relative to the patient, the fixed construction of conventional TMS apparatus significantly limits the character of the magnetic field which can be applied to the patient, and hence significantly limits the TMS therapy which can be provided to the patient. In addition, conventional TMS apparatus generally utilizes very high electric currents in the electromagnetic coil, which raises the risk of accidental injury to the patient through electric shocks, burns, seizures, etc.

The present invention addresses the foregoing problems associated with the prior art by providing an improved method and apparatus for providing Transcranial Magnetic Stimulation (TMS) to a patient. In addition, the present invention also provides additional advantages over conventional TMS, e.g., (a) it comprises a portable, wearable device that can be used outside of a medical or research facility, e.g., at home; (b) patients can self-administer a prescribed treatment regimen at home through handheld, or worn, wired or wireless electronic controllers; (c) it comprises multiple magnetic stimulators directable at multiple brain structures which can lead to better treatment, diagnostic testing or insight into brain function through its use in neuroscience research; (d) it comprises multiple magnetic stimulators directable at one and the same brain structure which can be more effective because they can induce current flow in multiple orientations; and (e) it comprises multiple magnetic stimulators which can aggregate their magnetic fields for more robust brain stimulation.

SUMMARY OF THE INVENTION

The present invention provides a novel method and apparatus for providing Transcranial Magnetic Stimulation (TMS) to a patient. Among other things, the present invention comprises the provision and use of novel TMS apparatus which allows the spatial, strength and temporal characteristics of the magnetic field generated by the TMS apparatus to be custom tailored for each patient, whereby to provide patient-specific TMS therapy or diagnostic testing. It also affords greater flexibility in open-ended investigations of brain function in neuroscience research.

In one form of the invention, there is provided apparatus for applying Transcranial Magnetic Stimulation (TMS) to a patient, wherein the apparatus comprises:
a head mount for disposition on the head of a patient; and
a plurality of magnet assemblies for releasable mounting on the head mount, wherein each of the magnet assemblies comprises a magnet for selectively providing a rapidly changing magnetic field capable of inducing weak electric currents in the brain of a patient so as to modify the natural electrical activity of the brain of the patient;
wherein the number of magnet assemblies mounted on the head mount, their individual positioning on the head mount, and their selective provision of a rapidly changing magnetic field is selected so as to allow the spatial, strength and temporal characteristics of the magnetic field to be custom tailored for each patient, whereby to provide patient-specific TMS therapy or diagnostic testing, as well as greater flexibility in open-ended investigations of brain function in neuroscience research. In one preferred form of the invention, each of the magnet assemblies comprises a magnet for selectively providing a rapidly changing magnetic field of at least 500-600 Tesla/second corresponding to a magnet movement speed of no less than 400 Hertz.

In another form of the invention, there is provided a method for providing Transcranial Magnetic Stimulation (TMS) to a patient, the method comprising:
providing apparatus comprising:
a head mount for disposition on the head of a patient; and
a plurality of magnet assemblies for releasable mounting on the head mount, wherein each of the magnet assemblies comprises a magnet for selectively providing a rapidly changing magnetic field capable of inducing weak electric currents in the brain of a patient so as to modify the natural electrical activity of the brain of the patient;
positioning the head mount on the head of the patient, and positioning a selected number of magnet assemblies on the head mount at selected locations; and
selectively providing a rapidly changing magnetic field with at least one of the magnet assemblies;
wherein the number of magnet assemblies mounted on the head mount, their individual positioning on the head mount, and their selective provision of a rapidly changing magnetic field is selected so as to custom tailor the spatial, strength and temporal characteristics of the magnetic field for that patient, whereby to provide patient-specific TMS therapy or diagnostic testing, as well as greater flexibility in open-ended investigations of brain function in neuroscience research. In one preferred form of the invention, each of the magnet assemblies comprises a magnet for selectively providing a rapidly changing magnetic field of at least 500-600 Tesla/second corresponding to a magnet movement speed of no less than 400 Hertz.

In another form of the invention, there is provided apparatus for applying Transcranial Magnetic Stimulation (TMS) to a patient, wherein the apparatus comprises:
a head mount for disposition on the head of a patient; and
a plurality of magnet assemblies mounted on the head mount in a predetermined pattern, wherein each of the magnet assemblies comprises a magnet for selectively providing a rapidly changing magnetic field capable of inducing weak electric currents in the brain of a patient so as to modify the natural electrical activity of the brain of the patient;

wherein the number of magnet assemblies mounted on the head mount, their individual positioning on the head mount, and their selective provision of a rapidly changing magnetic field is selected so as to allow the spatial, strength and temporal characteristics of the magnetic field to be custom tailored for each patient, whereby to provide patient-specific TMS therapy, to assist in diagnosis or to map out brain function in neuroscience research. In one preferred form of the invention, each of the magnet assemblies comprises a magnet for selectively providing a rapidly changing magnetic field of at least 500-600 Tesla/second corresponding to a magnet movement speed of no less than 400 Hertz.

In another form of the invention, there is provided a method for providing Transcranial Magnetic Stimulation (TMS) to a patient, the method comprising:

providing apparatus comprising:
a head mount for disposition on the head of a patient; and
a plurality of magnet assemblies mounted on the head mount in a predetermined pattern, wherein each of the magnet assemblies comprises a magnet for selectively providing a rapidly changing magnetic field capable of inducing weak electric currents in the brain of a patient so as to modify the natural electrical activity of the brain of the patient;
positioning the head mount on the head of the patient; and
selectively providing a rapidly changing magnetic field with at least one of the magnet assemblies;
wherein the number of magnet assemblies mounted on the head mount, their individual positioning on the head mount, and their selective provision of a rapidly changing magnetic field is selected so as to custom tailor the spatial, strength and temporal characteristics of the magnetic field for that patient, whereby to provide patient-specific TMS therapy, to assist in diagnosis or to map out brain function in neuroscience research. In one preferred form of the invention, each of the magnet assemblies comprises a magnet for selectively providing a rapidly changing magnetic field of at least 500-600 Tesla/second corresponding to a magnet movement speed of no less than 400 Hertz.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
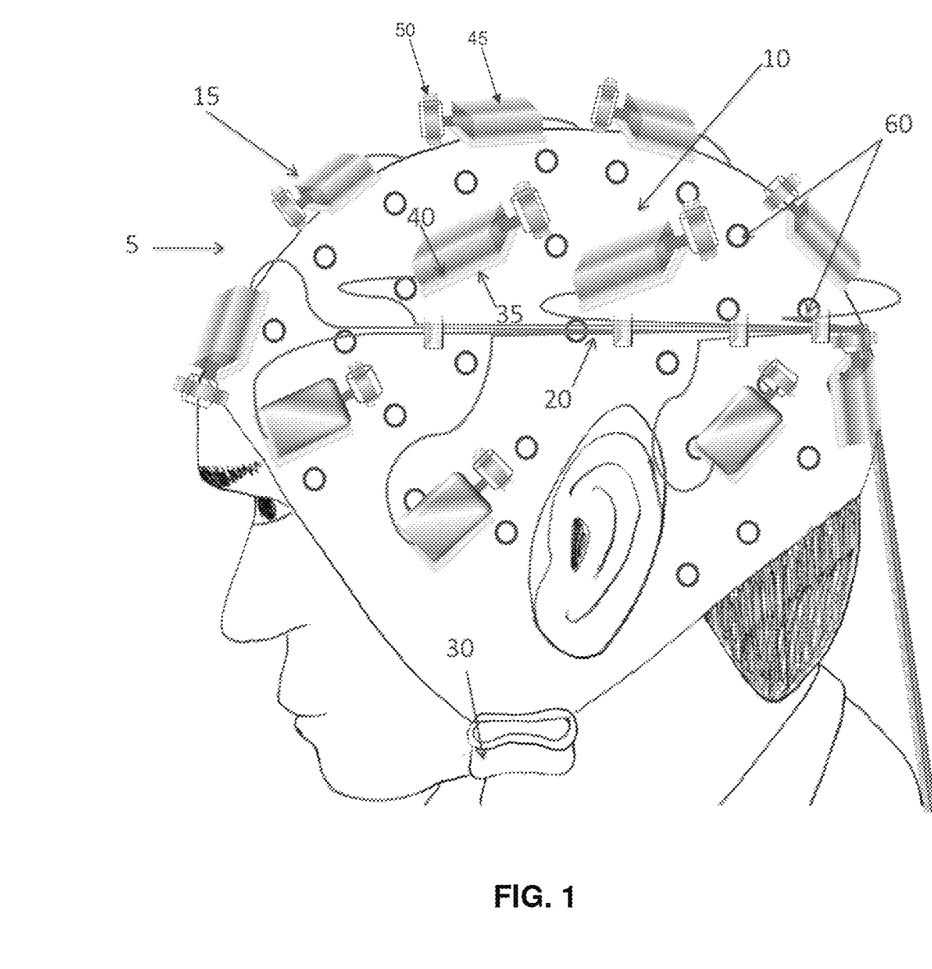
FIGS. 1 and 2 are schematic views illustrating novel apparatus for providing Transcranial Magnetic Stimulation (TMS) to a patient.
Figure 2:
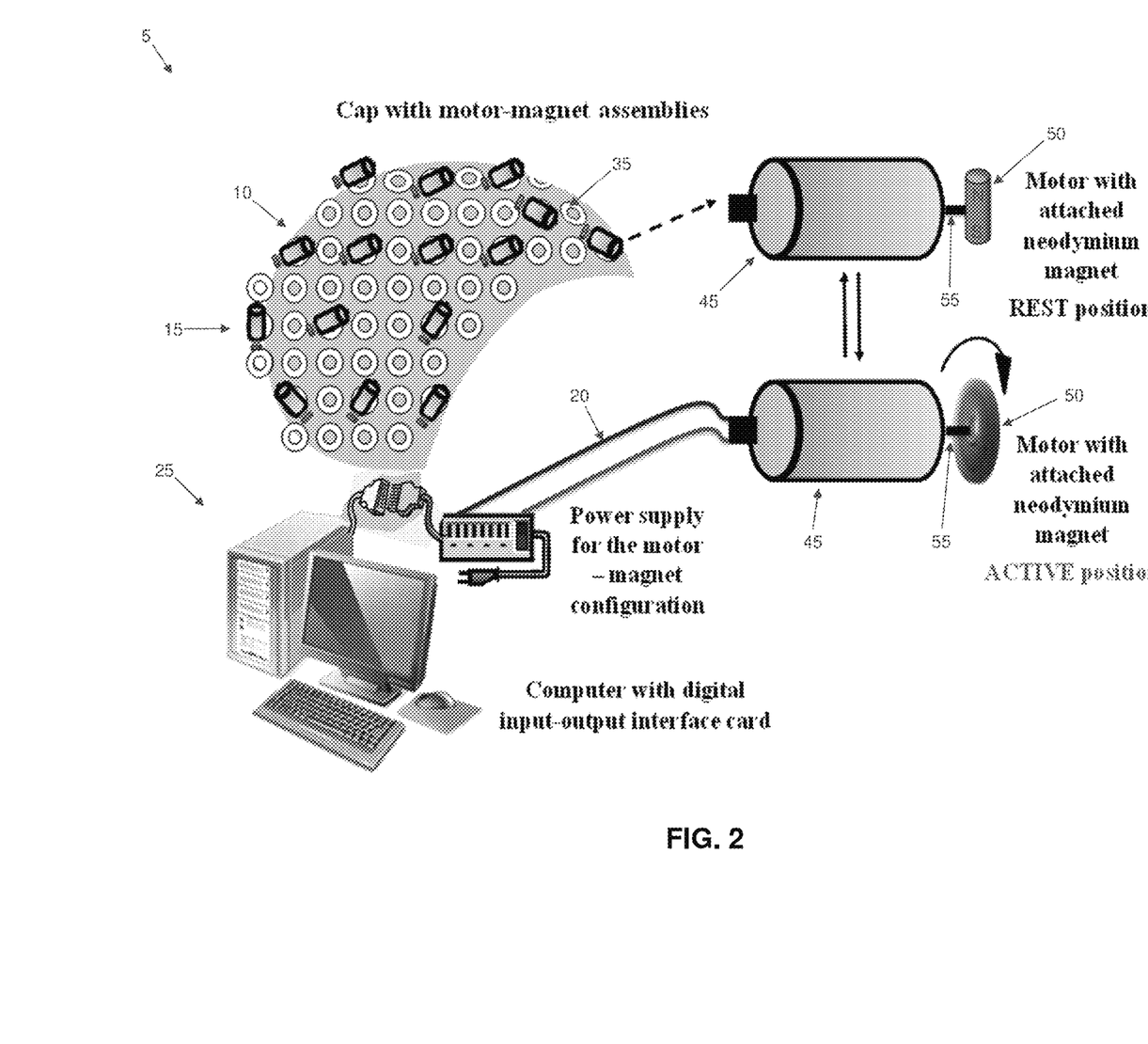

Looking first at FIGS. 1 and 2, there is shown novel Transcranial Magnetic Stimulation (TMS) apparatus 5 for providing TMS to a patient. Among other things, and as will hereinafter be discussed, novel TMS apparatus 5 allows the spatial, strength and temporal characteristics of the magnetic field generated by the TMS apparatus to be custom tailored for each patient, whereby to provide patient-specific TMS therapy, to assist in diagnosis or to map out brain function in neuroscience research.

More particularly, TMS apparatus 5 generally comprises a head mount 10 for positioning on the head of a patient, a plurality of magnet assemblies 15 which are releasably mounted to head mount 10, and a plurality of leads 20 for connecting each of the magnet assemblies 15 to a computerized controller 25. Computerized controller 25 may be a self-standing device or, if desired, computerized controller 25 may be wearable, e.g., on a waistband, an armband, etc. Additionally, if desired, magnet assemblies 15 may be connected to computerized controller 25 wirelessly, whereby to eliminate the need for leads 20.

In one preferred form of the invention, head mount 10 comprises a soft, form-fitting skull cap adapted to cover the head of the patient while leaving the face and ears of the patient exposed. Head mount 10 is intended to provide a stable support for the aforementioned magnet assemblies 15, and to that end head mount 10 preferably comprises a textile construct (e.g., woven, braided or knit fibers) that has a stable structure but which can breathe (for patient comfort). Alternatively, the head mount could be constructed of other materials such as soft plastic. Head mount 10 preferably includes a chin strap 30 so that the head mount can be fastened onto the head of a patient with light tension, whereby to ensure that the head mount maintains a fixed position on the head of the patient.

As noted above, a plurality of magnet assemblies 15 are releasably mounted to head mount 10. More particularly, magnet assemblies 15 are releasably mounted to head mount 10 so that the number of magnet assemblies 15, and/or their individual positioning on head mount 10, can be varied as desired by the clinician or investigator. To this end, head mount 10 preferably comprises a plurality of fastener bases 35 which are distributed about the outer surface of head mount 10, and each of the magnet assemblies 15 preferably comprises a counterpart fastener connect 40 adapted to mate with a fastener base 35, whereby to allow each magnet assembly 15 to be releasably secured to head mount 10 substantially anywhere about the surface of the head mount. It will be appreciated that, as a result of this construction, it is possible to releasably secure the desired number of magnet assemblies 15 to head mount 10, at the desired locations for those magnet assemblies 15, so that the number of magnet assemblies 15, and/or their positioning on head mount 10, can be varied as desired by the clinician or investigator.

By way of example but not limitation, head mount 10 may comprise a woven fabric skull cap covering the skull of the patient, the plurality of fastener bases 35 disposed on head mount 10 may each comprise one half of a conventional hook-and-loop (e.g., Velcro™) fastener, and the fastener connects 40 of the magnet assemblies 15 may each comprise the second half of a conventional hook-and-loop (e.g., Velcro™) fastener. In this way, each of the magnet assemblies 15 may be releasably fastened to a fastener base 35, and hence to head mount 10.

In one preferred form of the invention, magnet assemblies 15 each comprise a motor 45 and a permanent magnet 50. Permanent magnet 50 is mounted to the drive shaft 55 of motor 45, such that when motor 45 is energized, permanent magnet 50 will rotate, whereby to provide a rapidly changing magnetic field about the magnet assembly. In one preferred form of the invention, each of the magnet assemblies 15 comprises a permanent magnet 50 for selectively providing a rapidly changing magnetic field of at least 500-600 Tesla/second corresponding to a magnet movement speed of no less than 400 Hertz. As will be appreciated by those knowledgeable in the field of TMS, by applying this rapidly changing magnetic field of at least 500-600 Tesla/second, corresponding to magnet movement speed of no less than 400 Hertz, to the brain of a patient, weak electric currents can be induced in the neurons of the brain of the patient. These weak electric currents modify the natural electrical activity of the brain of the patient, whereby to provide therapy to the patient, to assist in diagnosis or to map out brain function in neuroscience research. In one preferred form of the invention, motor 45 is a variable speed motor, such that permanent magnet 50 may be rotated faster or slower, as desired, whereby to adjust the voltage of the electric currents induced in the neurons of the brain of the patient, as will hereinafter be discussed in further detail. In one preferred form of the invention, permanent magnet 50 comprises a rare earth magnet, e.g., a neodymium magnet.

TMS apparatus 5 also comprises a computerized controller 25 for independently controlling the operation of each of the magnet assemblies 15, i.e., turning motors 45 on or off, regulating the speeds of motor rotation, etc. Leads 20 connect computerized controller 25 to each of the magnet assemblies 15.

Figure 3:
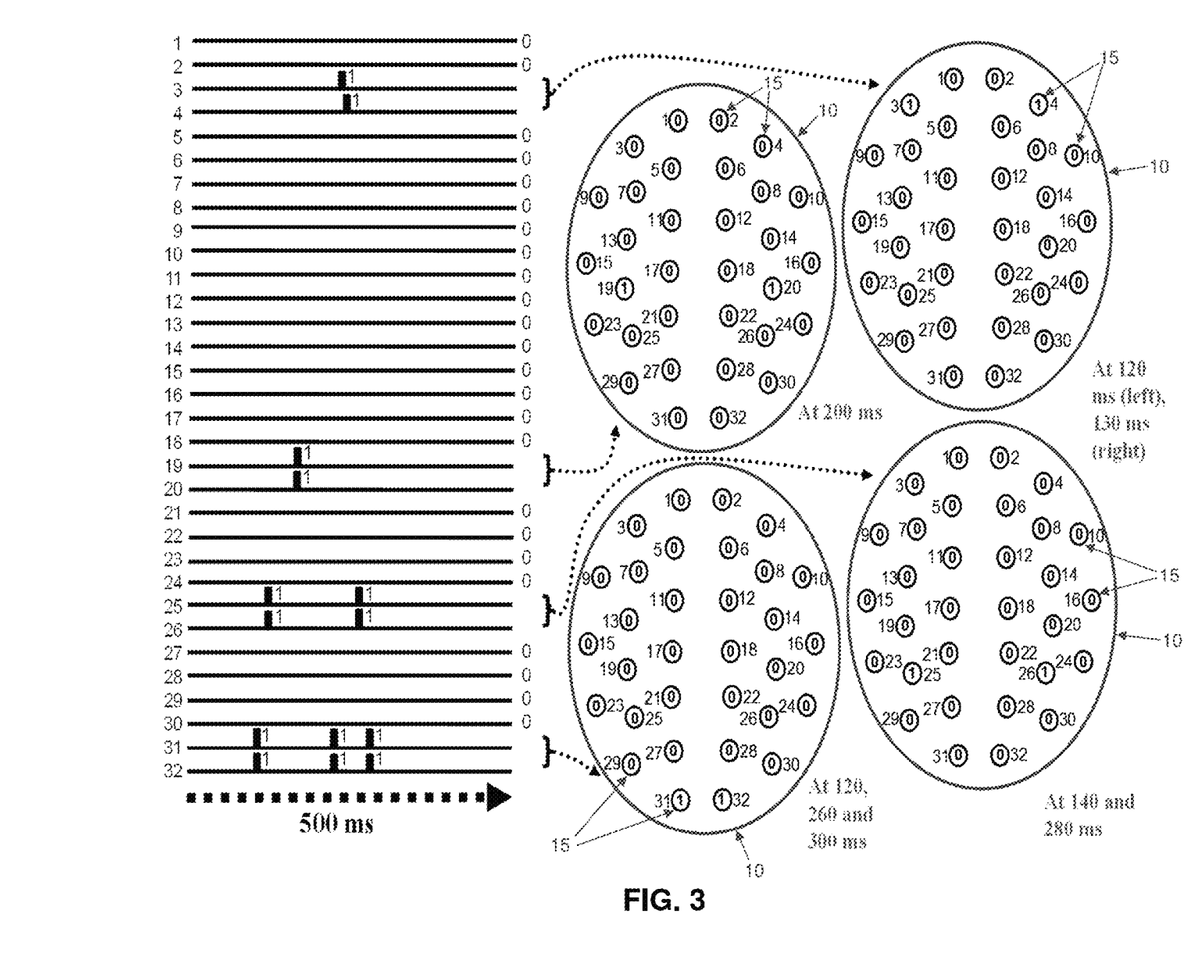
FIG. 3 is a schematic view illustrating how selective ones of the magnet assemblies of the TMS apparatus of FIGS. 1 and 2 may be activated at selected times so as to provide the desired TMS therapy to a patient, diagnostic testing or investigative protocol in neuroscience research.
Figure 4:
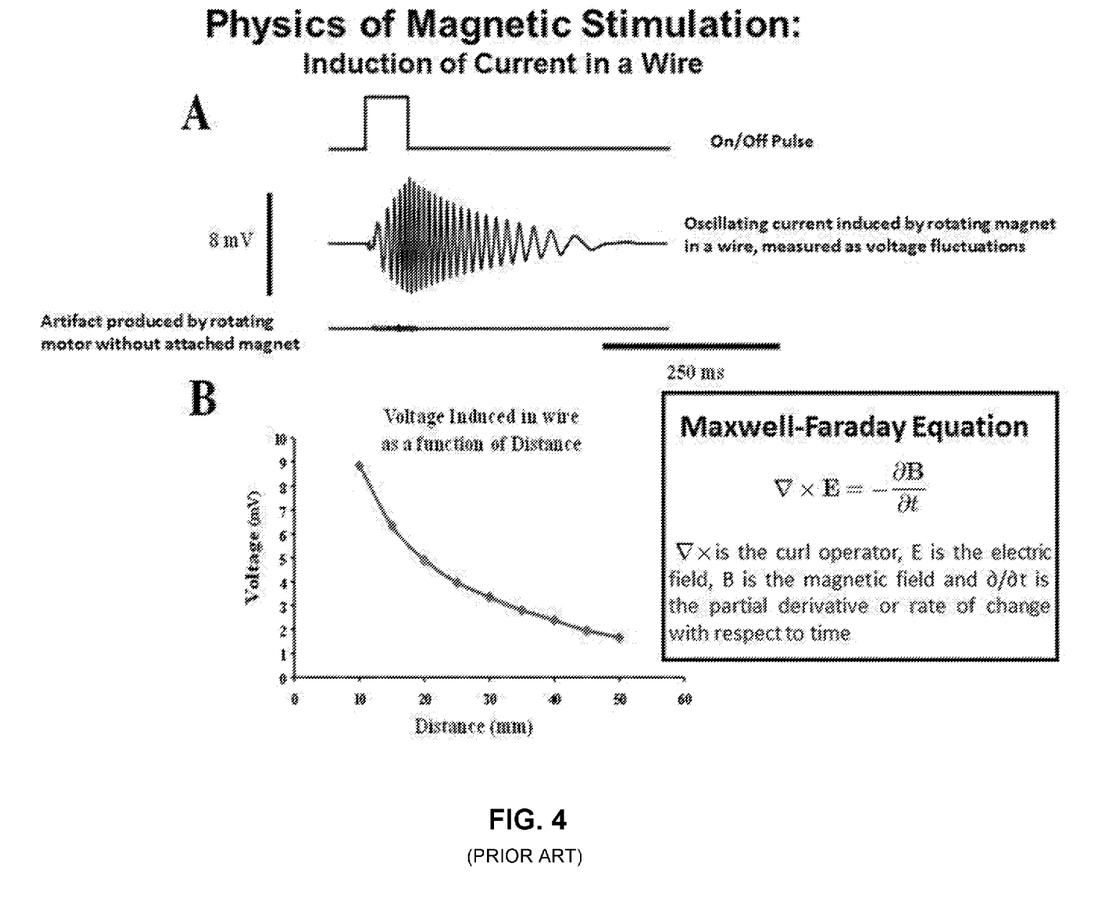
FIG. 4 is a schematic view illustrating the physics of magnetic stimulation in a conductor.
Figure 5:
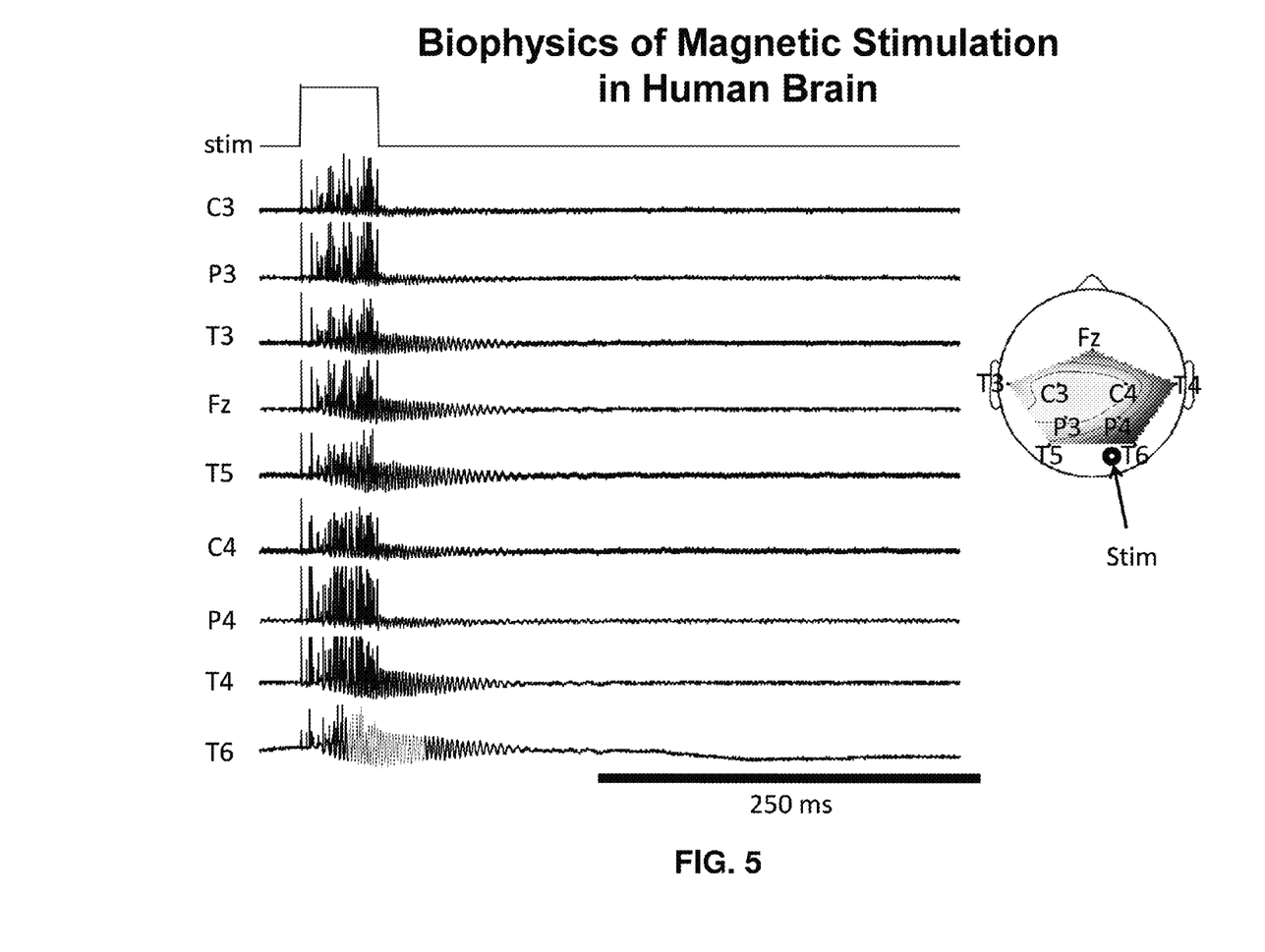
FIG. 5 is a schematic view illustrating the biophysics of magnetic stimulation of a brain.

Thus, in accordance with the present invention, a clinician or investigator first determines, for each individual patient, (i) how many magnet assemblies 15 should be mounted to head mount 10, (ii) where those magnet assemblies 15 should be mounted on head mount 10, (iii) when various magnet assemblies 15 should have their permanent magnets 50 rotated, and (iv) the speed of such rotation, in order to precisely tailor the spatial, strength and temporal characteristics of the magnetic field which is generated by TMS apparatus 5, whereby to provide that patient with patient-specific TMS therapy, to assist in diagnosis or to map out brain function in neuroscience research. Thereafter, when TMS therapy or test is to be applied to the patient, the patient puts on head mount 10, the clinician or investigator mounts the appropriate number of magnet assemblies 15 to head mount 10, positioning those magnet assemblies at the appropriate locations on head mount 10, and then computerized controller 25 thereafter controls which magnet assemblies 15 have their magnets rotated when, and at what speed. In this way, the spatial, strength and temporal characteristics of the magnetic field generated by TMS apparatus 5 can be precisely tailored according to each patient's needs, whereby to provide patient-specific TMS therapy to the patient, to assist in diagnosis or to map out brain function in neuroscience research. See, for example, FIG. 3, which shows how selected magnet assemblies 15, located at various locations about head mount 10, may have their respective permanent magnets rotated at different times. In this respect it will be appreciated that as the permanent magnet of a particular magnetic assembly 15 is rotated, it will apply a rapidly changing magnetic field to the patient, and this changing magnetic field is a function of the size and strength of the permanent magnet 50 of that magnet assembly and the rate at which the permanent magnet is rotated. See also, for example, FIG. 4, which illustrates the physics of magnetic stimulation in a conductor, and FIG. 5, which illustrates the rapid voltage fluctuations induced by magnetic stimulation in a human brain. Furthermore, it will be appreciated that the rapidly changing magnetic fields produced by the plurality of magnetic assemblies 15 located on head mount 10 together aggregate into a complex, composite, rapidly changing magnetic field which varies across the brain of the patient, both spatially and temporally, according to the positions of the magnet assemblies 15 on head mount 10 and the relative timings of their respective magnet rotations.

Thus it will be seen that with the novel TMS apparatus 5 of the present invention, the clinician or investigator may custom tailor the spatial, strength and temporal characteristics of the magnetic field generated by the TMS apparatus 5 for each patient, whereby to provide patient-specific TMS therapy, to assist in diagnosis or to map out brain function in neuroscience research.

Significantly, the present invention comprises a portable, wearable device that can be used outside of a medical or research facility, e.g., at home. Furthermore, patients can self-administer a prescribed treatment regimen at home through handheld, or worn, wired or wireless electronic controllers.

It should be appreciated that, inasmuch as the present invention comprises multiple magnetic stimulators directable at multiple brain structures, it can be possible to achieve better treatment, diagnostic testing or insight into brain function through its use in neuroscience research.

Also, inasmuch as the present invention comprises multiple magnetic stimulators directable at a single brain structure, it can be possible to achieve superior results because they can induce current flow in multiple orientations.

Furthermore, inasmuch as the present invention comprises multiple magnetic stimulators which can aggregate their magnetic fields for more robust brain stimulation, it can be possible to achieve better treatment, diagnostic testing or insight into brain function through its use in neuroscience research. Among other things, this more robust brain stimulation can relate to which regions of the brain are stimulated, the orientation(s) of the current flow induced in the regions which are stimulated, the magnitudes of the current flow induced in the regions which are stimulated, and the timings of such stimulation.

In accordance with the present invention, there is also provided a novel method for determining how many magnet assemblies 15 should be mounted to head mount 10, where those magnet assemblies 15 should be mounted on head mount 10, when various magnet assemblies 15 should have their magnets rotated, and the speed of such magnet rotation, in order to precisely tailor the spatial, strength and temporal characteristics of the magnetic field which is to be applied to that patient, whereby to provide that patient with patient-specific TMS therapy, to assist in diagnosis or to map out brain function in neuroscience research. More particularly, in accordance with the present invention, head mount 10 may include a plurality of electrodes 60 for monitoring changes in the electrical activity of the brain of the patient. Electrodes 60 are preferably connected to computerized controller 25 so that changes in the electrical activity of the brain, monitored by electrodes 60, can be correlated with variations in the spatial, strength and temporal characteristics of the magnetic field being applied to the patient by TMS apparatus 5, which in turn corresponds to the number, location and speed of rotation of the various magnet assemblies 15. In this way, using a feedback process, changes in the number, location and speed of rotation of the various magnet assemblies 15 can be correlated to changes in the electrical activity of the brain of the patient, whereby to create a patient specific TMS therapy, to assist in diagnosis or to map out brain function in neuroscience research.

The present invention offers numerous advantages over the prior art. More particularly, the novel TMS apparatus 5 of the present invention allows the spatial, strength and temporal characteristics of the magnetic field to be custom tailored for each patient, whereby to provide patient-specific TMS therapy, to assist in diagnosis or to map out brain function in neuroscience research. Among other things, the present invention provides the following significant advantages over conventional TMS: (a) it comprises a portable, wearable device that can be used outside of a medical or research facility, e.g., at home; (b) patients can self-administer a prescribed treatment regimen at home through handheld, or worn, wired or wireless electronic controllers; (c) it comprises multiple magnetic stimulators directable at multiple brain structures which can lead to better treatment, diagnostic testing or insight into brain function through its use in neuroscience research; (d) it comprises multiple magnetic stimulators directable at one and the same brain structure which can be more effective because they can induce current flow in multiple orientations; and (e) it comprises multiple magnetic stimulators which can aggregate their magnetic fields for more robust brain stimulation. In addition, the present invention eliminates the risk of accidental injury to the patient through electric shocks, burns, seizures, etc.

Figure 6:
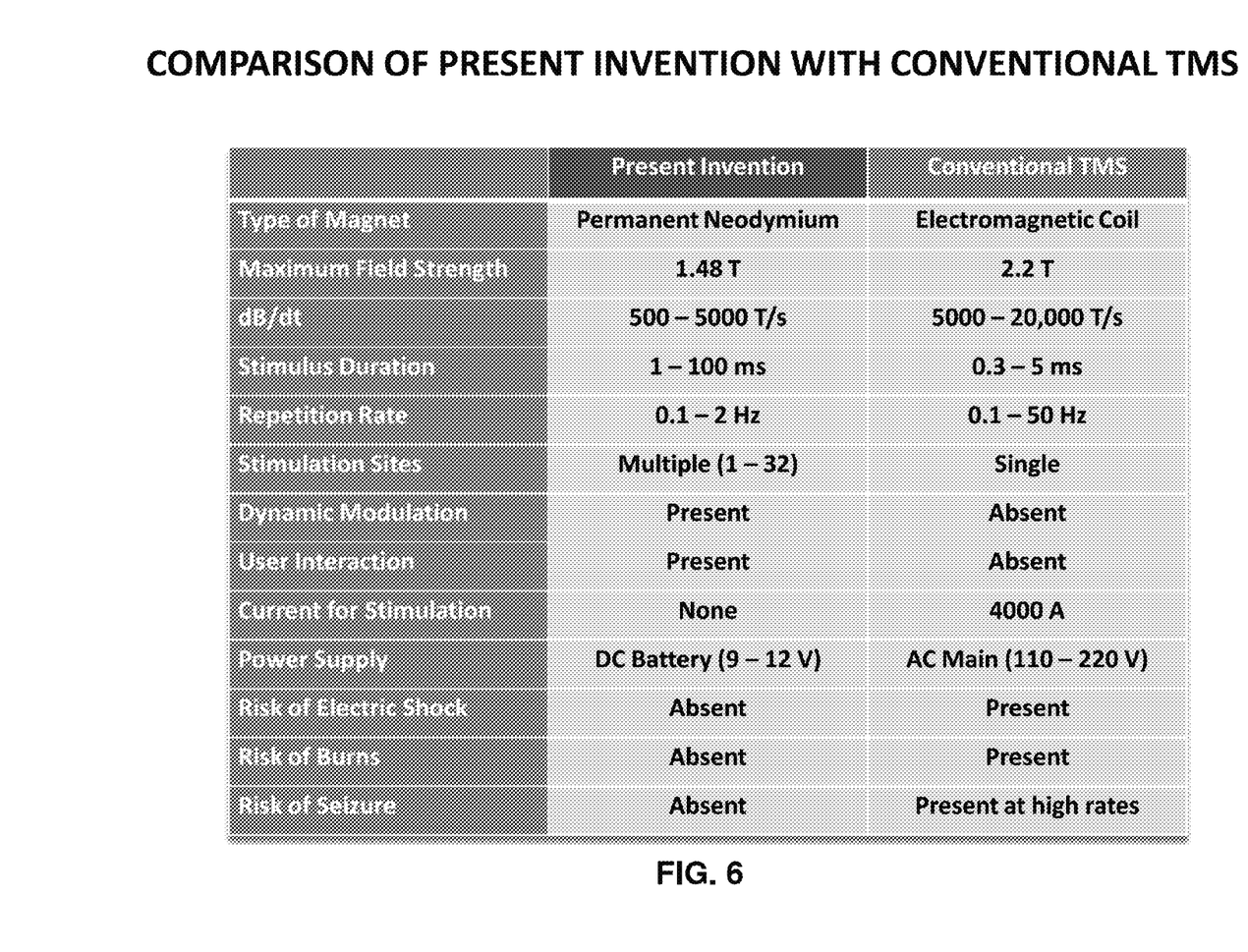
FIG. 6 is a table illustrating some of the advantages of the present invention over conventional TMS.

See FIG. 6, which lists some of the advantages of the present invention over conventional TMS apparatus.

Modifications of the Preferred Embodiments

It should be appreciated that many additional changes in the details, materials, steps and arrangements of parts, which have been herein described and illustrated in order to explain the nature of the present invention, may be made by those skilled in the art while still remaining within the principles and scope of the invention.

By way of example but not limitation, the entire outer surface of head mount 10 may be covered by a single large fastener base 35, or major sections of head mount 10 may be covered by several large fastener bases 35, where the one or more large fastener bases 35 receive one or more magnet assemblies 15.

Furthermore, if desired, head mount 10 may be formed as a harness, comprising a plurality of straps which are connected together, but have spacing between the various straps, so as to provide a grid-like structure about the head. These straps can be formed out of leather, plastic, a textile, etc. In this form of the invention, fastener bases 35, and hence magnet assemblies 15, are mounted along the straps which make up head mount 10.

Figure 7:
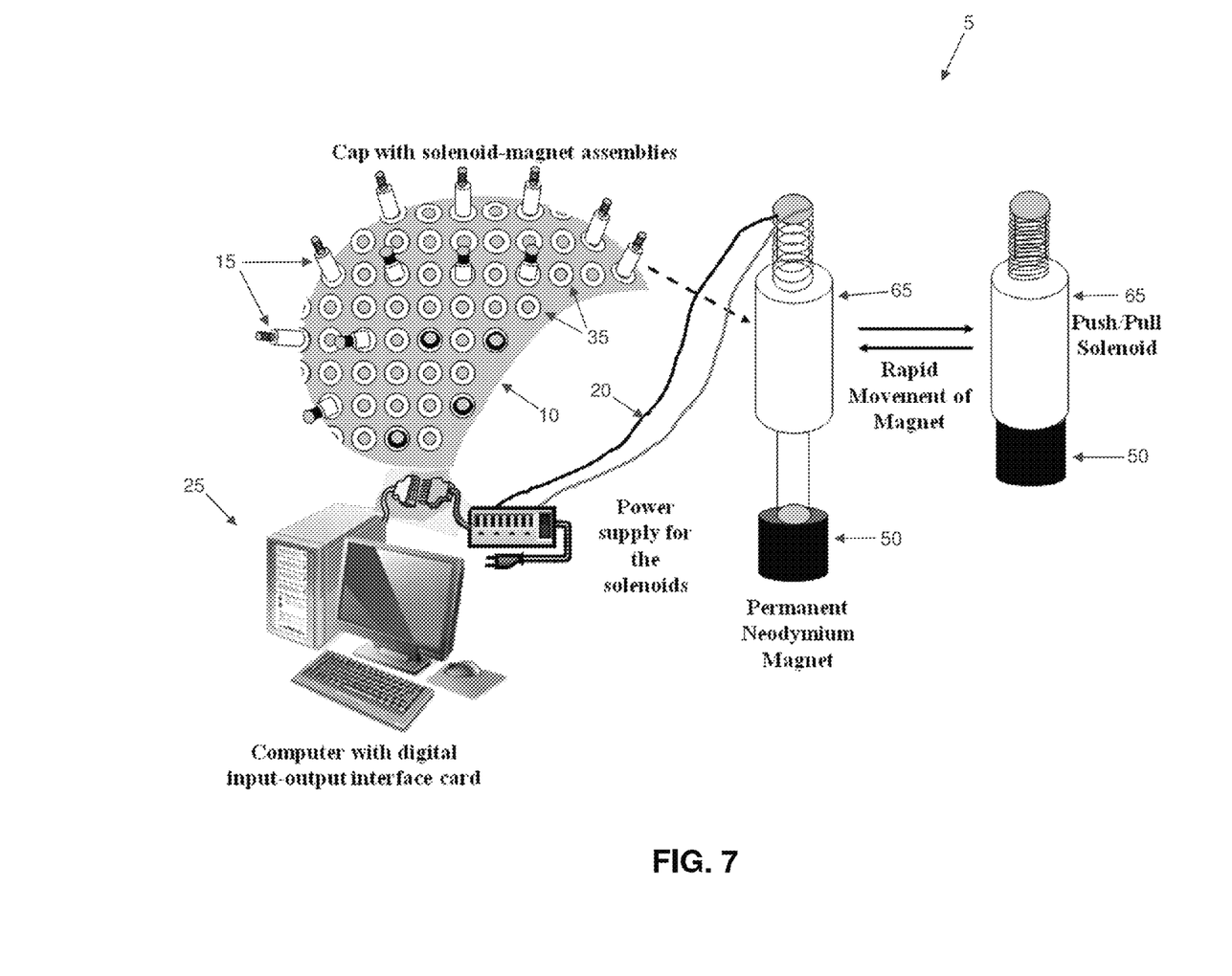
FIG. 7 is a schematic view illustrating alternative apparatus for providing TMS to a patient.

In addition, if desired, magnet assemblies 15 may be constructed so that magnets 50 are moved longitudinally, rather than rotationally, in order to produce a rapidly changing magnetic field. See, for example, FIG. 7, where solenoids 65 move magnets 50 rapidly so as to create the changing magnetic field utilized in the present invention.

Also, if desired, permanent magnets 50 may be replaced by small electromagnets, if the requisite high strength magnetic field can be achieved (e.g., so as to provide a rapid change of magnetic flux of at least 500-600 Tesla/second), and with the appropriate amount of cooling to prevent heating and melting of the magnet coils.

In accordance with the present invention, it is also possible to provide a head mount 10 (e.g., a skull cap) which has a predetermined number of magnet assemblies 15 already mounted on (or incorporated into) head mount 10 in a predetermined pattern. In this case, the clinician determines which ones of the predetermined, predisposed magnet assemblies 15 should be activated and, for those magnet assemblies which are to be activated, when they should have their magnets rotated, and the speed of such rotation, in order to precisely tailor the spatial, strength and temporal characteristics of the magnetic field which is to be applied to the patient, whereby to provide that patient with patient specific TMS therapy, to assist in diagnosis, or to map out brain function in neuroscience research. Furthermore, in this form of the invention, it may be desirable to provide a kit of such devices, wherein each device in the kit comprises a head mount 10 (e.g., a skull cap) which has a predetermined number of magnet assemblies 15 already mounted on (or incorporated into) head mount 10 in a predetermined pattern, with each device in the kit providing a different predetermined pattern of magnet assemblies 15.

These and other changes will be apparent to those skilled in the art in view of the present disclosure and are considered to be within the scope of the present invention.

What is claimed is:

1. An apparatus for applying Transcranial Magnetic Stimulation (TMS) to a patient, the apparatus comprising:
   a head mount for disposition on the head of the patient; and
   a plurality of magnet assemblies configured for releasable mounting on the head mount, wherein each of the magnet assemblies comprises a magnet for selectively providing a rapidly changing magnetic field capable of inducing weak electric currents in the brain of the patient so as to modify the natural electrical activity of the brain of the patient,
   wherein each of the magnet assemblies includes a permanent magnet and a motor for rotating the permanent magnet;
   a computerized controller configured to selectively activate the motor of at least one of the magnet assemblies to rotate the permanent magnet of that magnet assembly and thereby provide Transcranial Magnetic Stimulation (TMS) to the patient,
   wherein:
   (i) the computerized controller is configured to activate the motor to rotate the permanent magnet for a stimulus period of a given duration, and the stimulus period has a repetition rate of a given frequency, and
   (ii) during the stimulus period, the computerized controller is configured to activate the motor to rotate the permanent magnet at a particular rate to generate a particular stimulating pattern;
   wherein the number of magnet assemblies mounted on the head mount, their individual positioning on the head mount, and their selective provision of the rapidly changing magnetic field is selected to allow the spatial, strength and temporal characteristics of the Transcranial Magnetic Stimulation (TMS) to be custom tailored for the patient, whereby to provide patient-specific Transcranial Magnetic Stimulation (TMS) therapy, to assist in diagnosis or to map out brain function in neuroscience research;
   wherein the computerized controller is configured to activate the motor to rotate the permanent magnet at a frequency of at least 400 Hertz and provide a dB/dt of at least 500-600 Tesla/second; wherein the stimulus period has a duration of 1-100 milliseconds; and wherein the repetition rate of the stimulus period is 0.1 to 2 Hertz.

2. The apparatus according to claim 1 wherein the head mount comprises a skull cap.

3. The apparatus according to claim 1 wherein the magnet assemblies are secured to the head mount using a hook-and-loop fastener.

4. The apparatus according to claim 3 wherein the hook-and-loop fastener comprises a fastener base disposed on the head mount and a fastener connect disposed on each of the magnet assemblies.

5. The apparatus according to claim 1 wherein the permanent magnet comprises a rare earth magnet.

6. The apparatus according to claim 5 wherein the rare earth magnet comprises neodymium.

7. The apparatus according to claim 1 further comprising a plurality of electrodes for monitoring the electrical activity of the brain.

8. The apparatus according to claim 1 wherein the magnet assemblies are sized so that up to 32 magnet assemblies can be mounted to the head mount.

9. The apparatus according to claim 8 wherein the number of magnet assemblies mounted to the head mount is between 1 and 32.

10. Apparatus according to claim 1 wherein the permanent magnet has a maximum field strength of 1.48 Tesla.

11. A method for providing Transcranial Magnetic Stimulation (TMS) to a patient, the method comprising:
providing apparatus comprising:
a head mount for disposition on the head of the patient; and
a plurality of magnet assemblies for releasable mounting on the head mount, wherein each of the magnet assemblies comprises a magnet for selectively providing a rapidly changing magnetic field capable of inducing weak electric currents in the brain of the patient so as to modify the natural electrical activity of the brain of the patient;
wherein each of the magnet assemblies comprises a permanent magnet and a motor for rotating the permanent magnet;
positioning the head mount on the head of the patient, and positioning a selected number of magnet assemblies on the head mount at selected locations; and
selectively causing the motor of at least one of the magnet assemblies to rotate the permanent magnet of that magnet assembly and thereby provide a rapidly changing magnetic field with at least one of the magnet assemblies to provide Transcranial Magnetic Stimulation (TMS) to the patient, wherein:
(i) the motor rotates the permanent magnet for a stimulus period of a given duration, and the stimulus period has a repetition rate of a given frequency, and
(ii) during the stimulus period, the motor rotates the permanent magnet at a particular rate to generate a particular stimulating pattern;
wherein the number of magnet assemblies mounted on the head mount, their individual positioning on the head mount, and their selective provision of the rapidly changing magnetic field is selected so as to custom tailor the spatial, strength and temporal characteristics of the magnetic field for the patient, whereby to provide patient-specific TMS therapy, to assist in diagnosis or to map out brain function in neuroscience research;
wherein the motor rotates the permanent magnet at a frequency of at least 400 Hertz and provides a dB/dt of at least 500-600 Tesla/second;
wherein the stimulus period has a duration of 1-100 milliseconds; and
wherein the repetition rate of the stimulus period is 0.1 to 2 Hertz.

12. The method according to claim 11 wherein the head mount comprises a skull cap.

13. The method according to claim 11 wherein the magnet assemblies are secured to the head mount using a hook-and-loop fastener.

14. The method according to claim 13 wherein the hook-and-loop fastener comprises a fastener base disposed on the head mount and a fastener connect disposed on each of the magnet assemblies.

15. The method according to claim 11 wherein the permanent magnet comprises a rare earth magnet.

16. The method according to claim 15 wherein the rare earth magnet comprises neodymium.

17. A method according to claim 16 wherein the permanent magnet has a maximum field strength of 1.48 Tesla.

18. The method according to claim 11 further comprising a computerized controller for selectively causing selected ones of the magnet assemblies to provide a rapidly changing magnetic field.

19. The method according to claim 11 further comprising a plurality of electrodes for monitoring the electrical activity of the brain.

20. A method according to claim 11 wherein the magnet assemblies are sized so that up to 32 magnet assemblies can be mounted to the head mount.

21. A method according to claim 20 wherein the number of magnet assemblies mounted to the head mount is between 1 and 32.

* * * * *